United States Patent [19]
Kanayama et al.

[11] Patent Number: 5,798,389
[45] Date of Patent: Aug. 25, 1998

[54] GLOMERULONEPHRITIS INHIBITOR

[75] Inventors: Toshiji Kanayama; Taro Uchiyama; Isao Yanagisawa, all of Yokohama, Japan

[73] Assignee: Shiseido Co., Ltd., Tokyo, Japan

[21] Appl. No.: 719,231

[22] Filed: Sep. 25, 1996

[30] Foreign Application Priority Data

Sep. 26, 1995 [JP] Japan .................. 7-273557

[51] Int. Cl.$^6$ .................................. A61K 31/20
[52] U.S. Cl. .................................. 514/560
[58] Field of Search ........................ 514/560

[56] References Cited

U.S. PATENT DOCUMENTS 5,434,183  7/1995  Larsson-Backstrom ............ 514/549

FOREIGN PATENT DOCUMENTS

A-0 289 204  2/1988  European Pat. Off. .
4-273817  9/1992  Japan .
A-93 16691  2/1993  WIPO .

OTHER PUBLICATIONS

CA 115:235179, Latyshev et al., 1991.
CA 109:128397, Yamaguchi et al., 1988.
Dwight R. Robinson et al., J. Lipid. Res., vol. 34, no. 8, 1993.
Raffaele De Caterina et al., Kidney Int., vol. 44, No. 4, 1993.
Ralph T. Holman et al., Am. J. Kidney Dis., vol. 23, No. 5, 1994.
Charles Van Ypersele de Strihou, New Engl., J. Med., vol. 23, No. 5, 1994.

*Primary Examiner*—Kimberly Jordan
*Attorney, Agent, or Firm*—Ronald R. Snider

[57] ABSTRACT

A medicine effective in inhibiting glomerulonephritis is developed. A glomerulonephritis inhibitor contains, as an effective ingredient thereof, docosahexaenoic acid or a salt, ester, or amide thereof or other docosahexaenoic acid derivative.

13 Claims, 3 Drawing Sheets

GLOMERULONEPHRITIS INHIBITOR

RELATED APPLICATIONS

This application claims the priority if Japanese Patent Application No. Hei 7-273557 filed on Sep. 26, 1995, which is incorporated herein by reference.

FIELD OF THE INVENTION

The present invention relates to a glomerulonephritis inhibitor and, in particular, to development of a glomerulonephritis inhibitor comprising docosahexaenoic acid as an effective ingredient thereof.

BACKGROUND OF THE INVENTION

Glomerulonephritis is a typical autoimmune disease. In most cases thereof, an immune complex formed when an antigen, which is intravital foreign matter, and an antibody are combined together deposits on a glomerulus, thereby causing inflammation. Also, there are cases where an antibody which specifically recognizes a kidney tissue such as a basement membrane component in particular is generated within a body and bound to the kidney tissue, thereby causing inflammation. No effective method for treating glomerulonephritis has been reported yet.

Though hypochloric diet method, hypoprotein die method, and the like have currently been tried as a method for treating glomerulonephritis, no clear effects have been obtained. As a medicine therefor, only dipyridamole (Persantin), which is an antiplatelet drug, has been subjected to the Pharmaceutical Affairs Law, though with a low curative effect. Also, while steroid drugs are in use, they may generate side effects, rebound phenomenon, and so on. Further, among drugs such as steroids, some medicines administered for treatment may temporarily attain a high concentration in the kidney, thereby rather deteriorating nephritis. Also, since it takes a long period of time for treating glomerulonephritis, there has been a demand for developing a medicine which does not impose a heavy burden on patients.

SUMMARY OF THE INVENTION

In view of the foregoing problems of the prior art, it is an object of the present invention to provide a medicine which is effective in inhibiting glomerulonephritis.

As a result of diligent studies in view of the foregoing problems of the prior art, the inventors have found that docosahexaenoic acid can effectively function as a glomerulonephritis inhibitor, thereby accomplishing the present invention.

Namely, the glomerulonephritis inhibitor in accordance with the present invention contains, as an effective ingredient thereof, docosahexaenoic acid or a salt, ester, or amide thereof or other docosahexaenoic acid derivative.

The glomerulonephritis inhibitor of the present invention may contain, as an effective ingredient thereof, docosahexaenoic acid or a salt, ester, or amide thereof or other docosahexaenoic acid derivative having a purity of at least 90% as docosahexaenoic acid.

When used as an injection, the glomerulonephritis inhibitor is contained in sterile aqueous or nonaqueous solution, suspension and emulsion.

Also, when used as an internal medicine, the glomerulonephritis inhibitor is contained in a formulation carrier.

Further, the method of making a glomerulonephritis inhibitor in accordance with the present invention comprises the steps of crudely refining a fish oil to a purity of 50% to 60% as docosahexaenoic acid by iodine addition method; using liquid chromatography to further refine the crudely refined fish oil to yield docosahexaenoic acid or a salt, ester, or amide thereof or other docosahexaenoic acid derivative having a purity of at least 90% as docosahexaenoic acid; and then compounding thus refined product as an effective ingredient in the glomerulonephritis inhibitor.

Docosahexaenoic acid (referred to as "DHA" hereinafter) is a straight-chain hexaenoic acid having a carbon number of 22 with six double bonds. It is synthesized in vivo from $\alpha$-linolenic acid as a substrate. With respect to organism, DHA is expected to have functions of improving memory, suppressing decrease in visual acuity, and the like.

While the demand for its use in food has greatly increased in recent years, its development in medicine is still insufficient and desired. Specifically, the development thereof as therapeutic drugs for hyperlipemia, slight senile dementia, circulatory system diseases, allergic diseases, and the like has been expected.

As a drug using DHA, that disclosed in Japanese Unexamined Patent Publication No. Hei 4-273817 has been reported. This drug activates low density lipoprotein (referred to as "LDL" hereinafter) receptors in the liver and thereby decreases LDL cholesterol in plasma, while inhibiting the liver from producing endogenous cholesterol, and simultaneously decreases triglycerides in plasma. As this drug is administered, symptoms of hyperlipemia and the like can be improved, whereby diseases such as obesity, arteriosclerosis, cardiac coronary arterial diseases, ischemic heart disease, cerebral embolism, stroke, aneurysm, varix, thrombosis, and lower-limb arterial obstruction can be prevented and treated. Accordingly, as in the case of eicosapentaenoic acid (referred to as "EPA" hereinafter), DHA has been reported to be able to effectively function as a drug for treating hyperlipemia and arteriosclerosis.

As a large amount of DHA is contained in excitable cells such as brain, nerve cell, heart, retina, and spermatozoon, it is considered to inhibit abnormal excitation of the cells. On the other hand, a glomerulonephritis occurs due to abnormal excitation and growth of glomerular mesangial cells, taking DHA's effect of inhibiting abnormal cell excitation into account, the inventors have found DHA's effect of inhibiting glomerulonephritis.

Examples of DHA usable in the present invention include products refined from fish oils, as well as chemically synthesized products. Also, salts, esters, or amides of DHA which are tolerable as medicine can be used as DHA.

Examples of DHA salts usable in the present invention include salts of sodium and potassium. Example of DHA esters usable in the present invention include glyceride, ascorbic acid ester, sugar ester, and ethyl ester. Examples of DHA amides usable in the present invention include derivatives bound to amino acids, peptides, proteins, and the like by amide bonds.

Not only the above-mentioned salts, esters, and amides of DHA, but also other derivatives such as alcohols, amides, and dibasic acids which are converted into acids in vivo and tolerable as medicine can be used in the present invention.

In the present invention, the purity of DHA used is preferably at least 90% and more preferably at least 95%.

DHA in the present invention can be refined by a normally used method, for example, in which a fish oil is crudely refined by iodine addition method to a DHA purity of 50% to 60% and then liquid chromatography is used to further refine the crudely refined product to a DHA purity of 90% or higher.

The glomerulonephritis inhibitor of the present invention is typically used as internal medicine or injection.

When used as internal medicine, the glomerulonephritis inhibitor of the present invention may be orally administered as tablet, powder, granule, capsule, syrup, and the like; or parenterally administered as suppository and the like. Though the amount of administration depends on the degree of symptom, administration path, individual differences, age, form of drug, and the like; usually, as the amount of the effective ingredient itself, about 0.001 to 1 g/kg or, preferably, 0.01 to 0.5 g/kg is administered once or in several portions to an adult per day.

Formulation of the medicine is effected according to a normal method typically with a formulation carrier. When necessary, pharmacologically tolerable additives may be added thereto.

Namely, when a solid formulation for oral administration is to be prepared, an excipient is added to a main drug with further addition, when necessary, of binder, collapsing agent, lubricant, colorant, flavor-correcting agent, and the like; and then the resulting mixture is shaped into tablet, coated tablet, granule, powder, capsule and the like by a normal method.

Examples of the excipient include lactose, corn starch, saccharose, glucose, sorbitol, plasma cellulose, and silicon dioxide. Examples of the binder include polyvinyl alcohol, polyvinyl ether, ethyl cellulose, methyl cellulose, gum arabic, tragacanth, gelatin, shellac, hydroxypropyl cellulose, hydroxypropyl starch, and polyvinyl pyrrolidone. Examples of the collapsing agent include starch, agar, gelatin powder, crystalline cellulose, calcium carbonate, sodium hydrogen carbonate, calcium citrate, dextrin, and pectin. Examples of the lubricant include magnesium stearate, talc, polyethylene glycol, silica, and hardened vegetable oil. Examples of the colorant include those allowed to be added to medicines. Examples of the flavor-correcting agent include cocoa powder, menthol, aromatic acid, peppermint oil, borneol, and cinnamon powder. When necessary, sugar coating, gelatin coating, or other coating may be applied to the tablets and granules.

When the glomerulonephritis inhibitor of the present invention is used as injection, though the amount of administration depends on the degree of symptom, administration path, individual differences, age, form of drug, and the like; usually, as the amount of the effective ingredient itself, about 0.001 to 1 g/kg or, preferably 0.01 to 0.5 g/kg is administered once or in several portions to an adult per day.

The injection includes sterile aqueous or nonaqueous solution, suspension, and emulsion. In such an injection, at least one surfactant is used while being mixed with at least one inactive aqueous diluent or inactive nonaqueous diluent. Further, when necessary, it may contain adjuvants such as antiseptic, wetting agent, emulsifier, dispersant, stabilizer, and solubilizer. These ingredients are normally turned into a solid composition after filtering (through a bacteria-retaining filter or the like), compounding of disinfectant therein, or irradiation with gamma rays; and then sterile water or sterile injection diluent is added thereto immediately before use.

DETAILED DESCRIPTION OF THE PREFERRED EMBODIMENTS

In the following, embodiments of the present invention will be explained in further detail.

Rats were used to investigate effects of DHA on glomerulonephritis.

Experimental Animal (see FIG. 1)
[Method of Preparation]

Five-week-old male SD-strain rats were used to perform an experiment.

First, 3 mg/kg of RSA (rabbit serum albumin) suspended in a complete adjuvant (Freund) were subcutaneously administered to each rat. This administration was repeated every two weeks for three times. Thus, an antibody was generated within the rat body.

From the sixth week after the starting of the experiment, 2 mg/kg of RSA dissolved in physiological saline solution were intravenously administered to the rat three times per week. This administration was repeated till the fourteenth week after the starting of the experiment. Thus, an antigen-antibody complex was generated within the rat body, thereby yielding a glomerulonephritis model rat.

According to the foregoing method, an antigen against a foreign protein is initially formed within the rat body as a result of the three shots of RSA subcutaneous injections affected by the sixth week after the starting of the experiment. Then, as RSA, which is an antigen, is repeatedly intravenously injected, a large amount of an antigen-antibody complex (IC) is generated within the rat body. This IC has a characteristic of specifically depositing on granular mesangial cells. Thus, due to the stickiness in platelets and activation and wetting of leucocytes caused by the IC, secretion of cytokines increases. Since thus secreted cytokines include a factor for accelerating cell proliferation, mesangial cells start to proliferate. As they proliferate in excess, construction of glomeruli is damaged, subsequently lowering functions of the kidney, discharging urinary protein, generating nephritis, and advancing the symptom. This process is similar to that of generation of human glomerulonephritis. Accordingly, a suitable model rat for glomerulonephritis is obtained.

Figure 1:
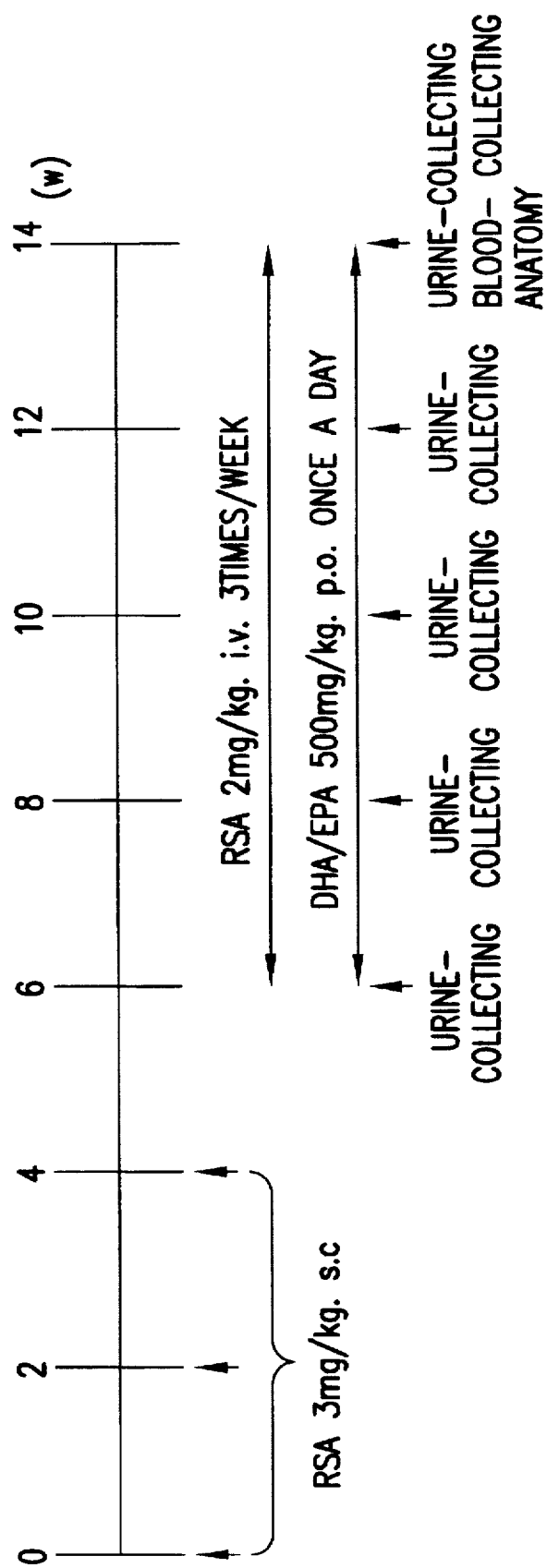
FIG. 1 is an explanatory view showing the procedure of an experiment in the present invention.

Method of Experiment (see FIG. 1)

From the sixth week after the starting of the experiment, simultaneously with the intravenous injection of RSA, the experimental animals were divided into three groups, and drugs listed in Table 1 were orally administered thereto once a day. Here, each of DHA and EPA was used with a purity of at least 90%.

TABLE 1

|  | Group 1 | Group 2 | Group 3 |
| --- | --- | --- | --- |
| DHA (mg/day) | 0 | 500 | 0 |
| EPA (mg/day) | 0 | 0 | 500 |

At the sixth, eighth, tenth, twelfth, and fourteenth weeks after the starting of the experiment, urine was collected from each experimental animal, and urinary protein was measured. Also, at the tenth and fourteenth week, urinary creatinine was measured. Further, at the fourteenth week after the starting of the experiment, blood was collected from the experimental animal, blood creatinine was measured, the kidney was removed from the animal by dissection, and thus removed kidney was immobilized by formalin.

Results

Figure 2:
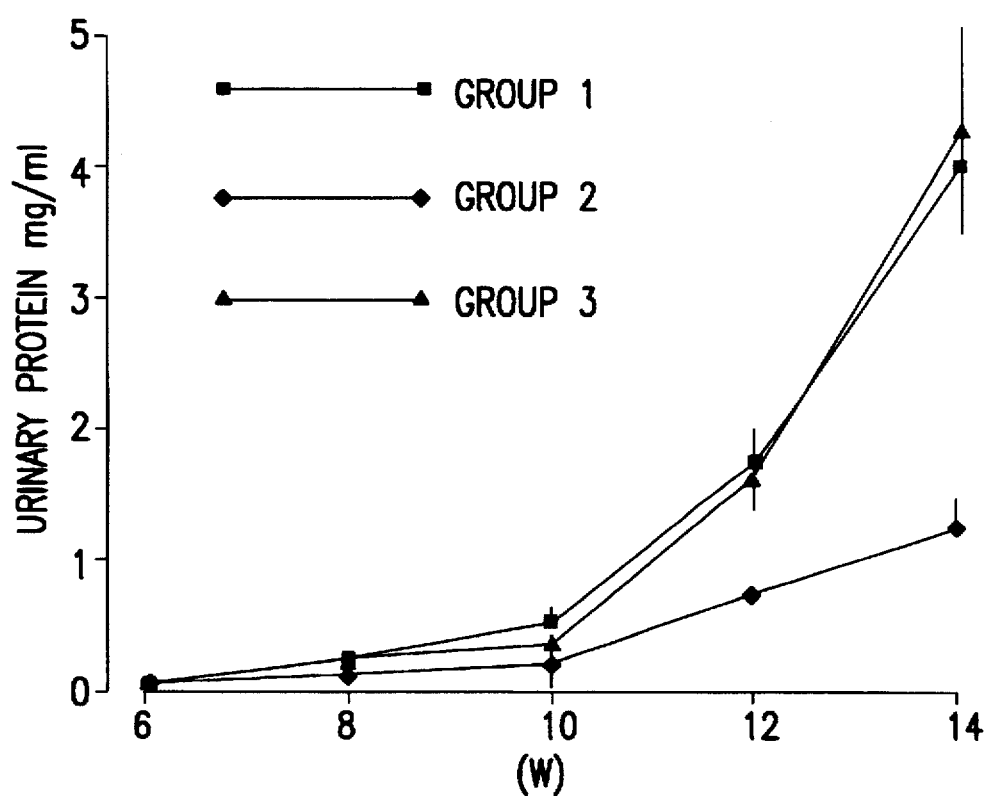
FIG. 2 is an explanatory view showing the amount of urinary protein at the sixth to fourteenth week after the starting of the experiment.
Figure 3:
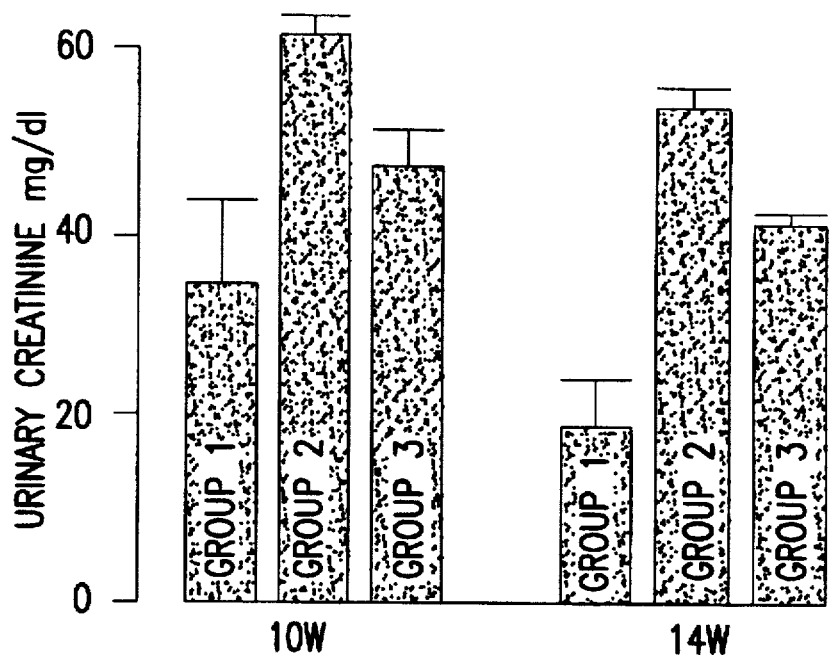
FIG. 3 is an explanatory view showing the amount of urinary creatinine at the tenth and fourteenth weeks after the starting of the experiment.
Figure 4:
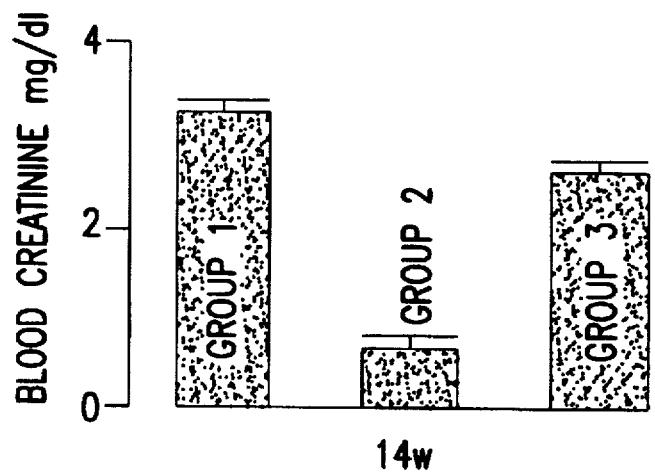
FIG. 4 is an explanatory view showing the amount of blood creatinine at the fourteenth week after the starting of the experiment.

FIGS. 2 to 4 respectively show the results of measurement of urinary protein, urinary creatinine, and blood creatinine. Urinary protein tends to increase as functions of the kidney lower. Also, urinary and blood creatinine amounts may become a fine marker of functions of glomeruli.

Urinary Protein Amount

As can be seen from FIG. 2, while urinary protein increases with time from the eighth week after the starting of the experiment in Group 1, which is a control, and Group 3 to which EPA was administered; it increases moderately in Group 2 to which DHA was administered.

Namely, at the fourteenth week, while the amount of urinary protein is 3.96±0.49 mg/ml in Group 1, it is 1.25±0.22 mg/ml in Group 2, which has been suppressed to ⅓ or less of the former. Group 3, which is an EPA-administered group, exhibits a progress substantially the same as that of Group 1, without any decrease in urinary protein.

Measurement of Creatinine Concentration

Urinary creatinine decreases as functions of glomeruli lower. As can be seen from FIG. 3, while amounts of urinary creatinine at the tenth and fourteenth weeks are respectively 37.5±6.1 mg/dl and 18.5±5.0 mg/dl in Group 1, they are respectively 61.1±1.5 mg/dl and 53.0±2.3 mg/dl in Group 2 which is a DHA-administered group. Here, since the amount of urinary creatinine in a normal rate is 106.6±5.0 mg/dl, the ratio of its decrease in Group 2 is significantly lower than that in Group 1.

Also, blood creatinine increases as functions of glomeruli lower. As can be seen from FIG. 4, while the amount thereof is 3.25 mg/dl in Group 1, Group 2 exhibits a value of 0.66±0.01 mg/dl which is quite low.

In Group 3, on the other hand, though significant differences are seen in the urinary and blood creatinine amounts at the fourteenth week, they exhibit slighter changes as compared with Group 2.

Further, as DHA is a component within an organism, it is considered to be highly safe. A drug temporarily attains a very high concentration in a uriniferous tubule in the process of being reabsorbed by the kidney. Accordingly, many kinds of drugs exhibit renal toxicity regardless of their fields. There may be cases where a drug administered in order to treat nephritis rather deteriorates the condition of the disease. This possibility is deemed to be low in DHA. The rat model realized herein is a system similar to generation of glomerulonephritis in human. Since DHA exhibited remarkable effects in this system, high therapeutic effects are clinically expected.

As can be seen from the foregoing results, increases in amounts of urinary protein and blood creatinine can be suppressed when DHA is administered. Accordingly, it is suggested that deterioration of glomerulus function-kidney function has been significantly suppressed.

In the following, preferred examples of the present invention will be shown. The present invention should not be restricted to these examples of formulation, however.

EXAMPLE 1

Tablet

To 100 mg of DHA, 100 mg of lactose, 30 mg of corn starch, 80 mg of talc, and 2 mg of magnesium stearate were added and mixed together. The resulting mixture was formed into tablets.

When an enteric coated drug was to be made, each of the tablets was coated with an enteric coating of hydroxypropylmethyl cellulose naphthalate.

EXAMPLE 2

Capsule Drug

To 50 mg of DHA, 100 mg of corn starch, 150 mg of lactose, and 1 mg of light silicic anhydride were added and mixed together. The resulting mixture was filled into a No. 2 gelatin hard capsule. When an enteric coated capsule was to be made, the capsule was coated with an enteric coating of hydroxypropylmethyl cellulose naphthalate.

EXAMPLE 3

Injection

DHA was dissolved into the Japanese Pharmacopoeia physiological saline solution at a ratio of 10 mg per 10 ml. The resulting solution was filtered through a membrane filter in a sterile manner. The filtrate was dispensed into immunized ampule bottles, which were then heat-sealed.

What is claimed is:

1. A method for inhibiting glomerulonephritis comprising:
   administering to a host of a therapeutically effective amount of docosahexaenoic acid or a docosahexaenoic acid derivative.

2. The method for inhibiting glomerulonephritis according to claim 1, wherein said docosahexaenoic acid or said docosahexaenoic acid derivative has a purity of at least 90% as docosahexaenoic acid.

3. The method for inhibiting glomerulonephritis according to claim 1, wherein said docosahexaenoic acid derivative is selected from the group consisting of a salt form, an ester form, and an amide form of docosahexaenoic acid.

4. The method for inhibiting glomerulonephritis according to claim 1, wherein said salt form of docosahexaenoic acid consists of salts of sodium or potassium.

5. The method for inhibiting glomerulonephritis according to claim 1, wherein said ester form of docosahexaenoic acid is selected from the group consisting of glyceride ester, ascorbic acid ester, sugar ester, and ethyl ester.

6. The method for inhibiting glomerulonephritis according to claim 1, wherein said amide form of docosahexaenoic acid is selected from the group consisting of amino acid, peptide, and protein.

7. The method for inhibiting glomerulonephritis according to claim 1, wherein said docosahexaenoic acid or said docosahexaenoic acid derivative is administered via parenteral injection.

8. The method for inhibiting glomerulonephritis according to claim 7, wherein said docosahexaenoic acid or said docosahexaenoic acid derivative is contained in sterile aqueous solution, sterile nonaqueous solution, suspension, or emulsion.

9. The method for inhibiting glomerulonephritis according to claim 7, wherein said docosahexaenoic acid or said docosahexaenoic acid derivative is administered in the amount of 0.001 to 1 g/kg to an adult per day.

10. The method for inhibiting glomerulonephritis according to claim 1, wherein said docosahexaenoic acid or said docosahexaenoic acid derivative is orally administered.

11. The method for inhibiting glomerulonephritis according to claim 10, wherein said docosahexaenoic acid or said docosahexaenoic acid derivative is orally administered as tablet, powder, granule, capsule, or syrup.

12. The method for inhibiting glomerulonephritis according to claim 10, wherein said docosahexaenoic acid or said docosahexaenoic acid derivative is orally administered in the amount of 0.001 to 1 g/kg to an adult per day.

13. The method for inhibiting glomerulonephritis according to claim 10, wherein said docosahexaenoic acid or said docosahexaenoic acid derivative is contained in a formulation carrier.

* * * * *